US011162903B2

(12) United States Patent
Kawabe et al.

(10) Patent No.: US 11,162,903 B2
(45) Date of Patent: Nov. 2, 2021

(54) APPARATUS, SYSTEM, AND METHOD FOR LUMINESCENCE MEASUREMENT

(71) Applicant: HITACHI, LTD., Tokyo (JP)

(72) Inventors: Shunsuke Kawabe, Tokyo (JP); Yuichi Uchiho, Tokyo (JP); Hideyuki Noda, Tokyo (JP)

(73) Assignee: HITACHI, LTD., Tokyo (JP)

( * ) Notice: Subject to any disclaimer, the term of this patent is extended or adjusted under 35 U.S.C. 154(b) by 34 days.

(21) Appl. No.: 16/740,048

(22) Filed: Jan. 10, 2020

(65) Prior Publication Data

US 2020/0240921 A1    Jul. 30, 2020

(30) Foreign Application Priority Data

Jan. 25, 2019   (JP) .............................. JP2019-011323

(51) Int. Cl.
*G01N 21/76* (2006.01)
*G01N 35/02* (2006.01)
(Continued)

(52) U.S. Cl.
CPC ............. *G01N 21/76* (2013.01); *G01N 21/11* (2013.01); *G01N 21/6452* (2013.01);
(Continued)

(58) Field of Classification Search
CPC .. G01N 21/76; G01N 35/1011; G01N 35/109; G01N 21/6452; G01N 21/11;
(Continued)

(56) References Cited

U.S. PATENT DOCUMENTS 4,944,922 A  *  7/1990  Hayashi ............. G01N 35/1009
                                                      356/624
5,290,513 A  *  3/1994  Berthold ................ G01N 21/76
                                                      250/328
(Continued)

FOREIGN PATENT DOCUMENTS

EP       0136002 A2  *  4/1985  ........... G01N 21/253
EP       3290909 A1     3/2018
(Continued)

OTHER PUBLICATIONS

Translation of JPH06213905A, Tajima, Hideji, Aug. 5, 1994 (Year: 1994).*

(Continued)

*Primary Examiner* — Samuel P Siefke
*Assistant Examiner* — Henry H Nguyen
(74) *Attorney, Agent, or Firm* — Procopio, Cory, Hargreaves & Savitch LLP

(57) ABSTRACT

An apparatus, system, and method for performing an efficient luminescence measurement are disclosed. The apparatus comprises a nozzle for dispensing a luminescent reagent into a well W in a microplate M, a luminescence measurement unit for measuring luminescence occurring in the well W caused by mixing of the luminescent reagent and a specimen, and a stage (moving unit) for moving the nozzle and the luminescence measurement unit together vertically and horizontally, wherein the nozzle is secured to the stage and the luminescence measurement unit is mounted to be movable vertically with respect to the stage through a holder and springs interposed between the luminescence measurement unit and the holder.

5 Claims, 14 Drawing Sheets

(51) Int. Cl.
  *G01N 21/11* (2006.01)
  *G01N 35/10* (2006.01)
  *G01N 21/64* (2006.01)
  *G01N 33/58* (2006.01)

(52) U.S. Cl.
  CPC ......... *G01N 35/028* (2013.01); *G01N 35/109* (2013.01); *G01N 35/1011* (2013.01); *G01N 33/582* (2013.01)

(58) Field of Classification Search
  CPC .. G01N 35/028; G01N 33/582; G01N 21/253; G01N 2035/1076; G01N 35/00732
  See application file for complete search history.

(56) References Cited

U.S. PATENT DOCUMENTS

| | | | |
|---|---|---|---|
| 5,798,263 A | | 8/1998 | Wood et al. |
| 2014/0051083 A1* | | 2/2014 | Tajima ................... C12Q 1/686 435/6.12 |
| 2019/0195807 A1 | | 6/2019 | Lansing et al. |

FOREIGN PATENT DOCUMENTS

| | | | | |
|---|---|---|---|---|
| JP | H06213905 A | * | 8/1994 | |
| JP | 2015175707 A | | 10/2015 | |
| WO | WO-2015030368 A1 | * | 3/2015 | ............ G01N 35/10 |
| WO | 2018033600 A1 | | 2/2018 | |

OTHER PUBLICATIONS

Translation of WO2015030368A1, Kim, Kyungnam, Mar. 5, 2015 (Year: 2015).*
Extended European Search Report for related European Application No. 20150859.5, dated Jul. 8, 2020 (8 pages).
Navigator System Operating Manual Instructions for Use of Products GM2000 and GM2010 (Online), GloMax, Retrieved on Dec. 28, 2018) Internet <URL: https://www.promega.jp/-/media/files/resources/protocols/technical-manuals/101/glomax-navigator-system-operating-manual.pdf?la=en>.

* cited by examiner

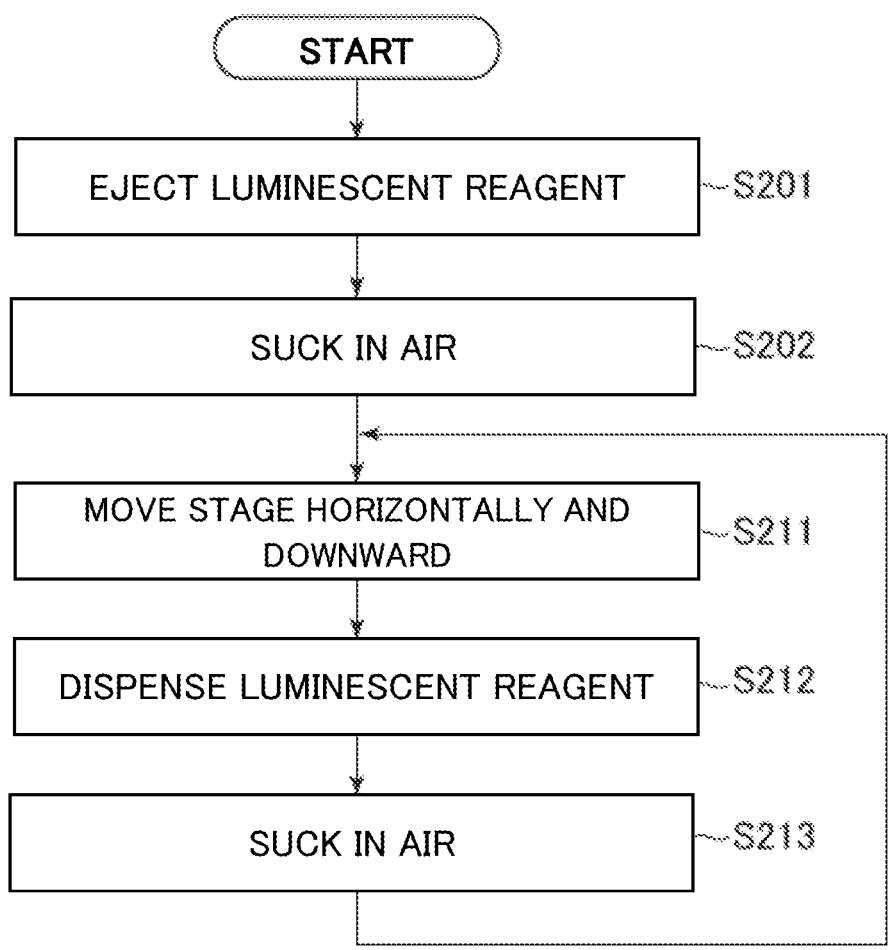

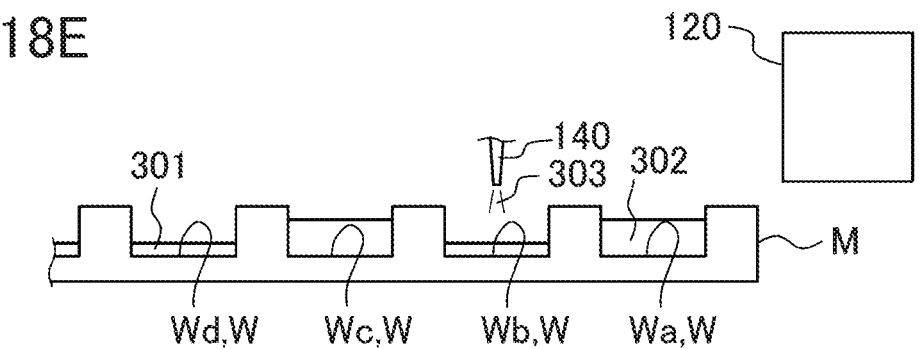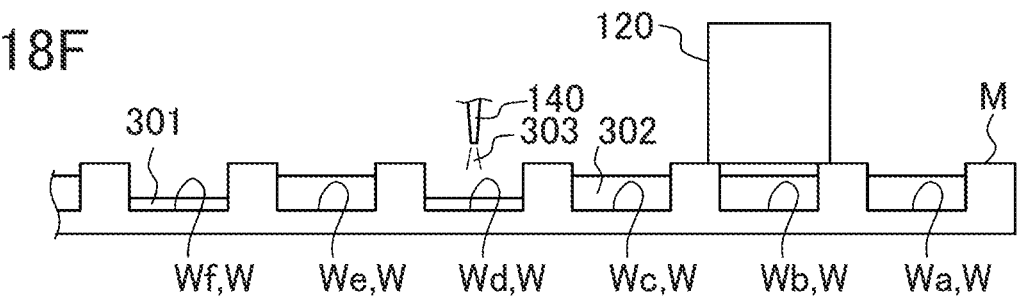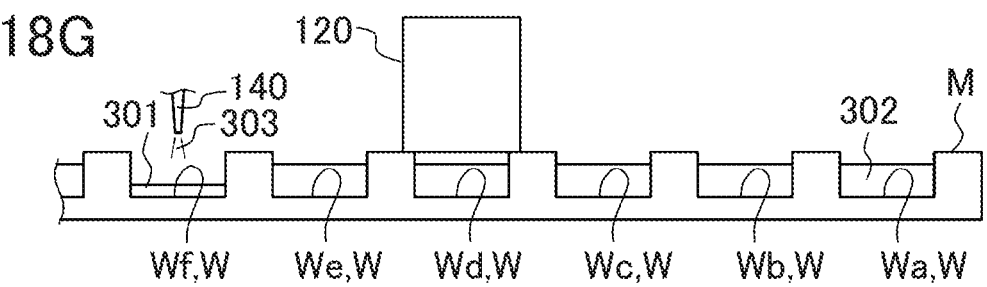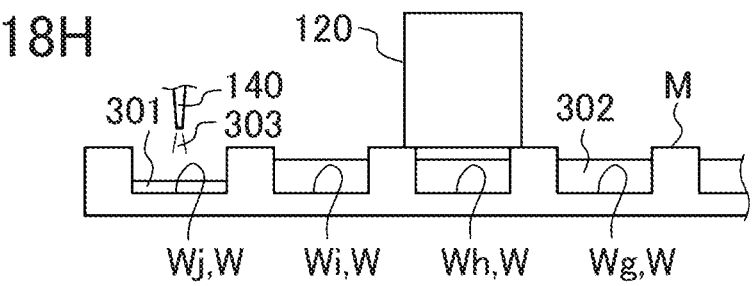

APPARATUS, SYSTEM, AND METHOD FOR LUMINESCENCE MEASUREMENT

CROSS REFERENCE TO RELATED APPLICATIONS

The present invention relates to and asserts priority from Japanese patent application No. 2019-011323 filed on Jan. 25, 2019, and incorporates the entirely of the contents and subject matter of all the above application herein by reference.

TECHNICAL FIELD

The present invention relates to a technology on an apparatus, a system, and a method for luminescence measurement.

BACKGROUND ART

Mixing a specimen and a luminescent reagent in a microplate causes chemiluminescence and, evaluating an amount of the luminescence allows to obtain biological information of the specimen. To detect such a luminescence at higher sensitivity, a Photomultiplier Tube (PMT) is generally often used as a luminescence detector. Further, in most cases, dispensing a luminescent reagent and measuring luminescence are performed in the same apparatus, and both a dispensing mechanism and a measuring mechanism are mounted together in the same apparatus.

Vertical positioning of a nozzle that is used to dispense a luminescent reagent is performed according to a specimen, a type of a luminescent reagent, its liquid surface level, and a shape of a microplate. Further, the photosensitive surface of a photomultiplier tube can receive light at higher sensitivity as positioned closer to a luminous point, and therefore, the photomultiplier tube is generally positioned as close to the microplate as possible to perform luminescence measurement.

A chemiluminescence measurement apparatus using a luminescent reagent called "flash type" requires performing luminescence measurement as early as possible (typically, within several seconds) after mixing a luminescent reagent and a specimen. To do so, it is desirable to arrange a nozzle for dispensing the luminescent reagent and a photomultiplier tube for measuring luminescence as close to each other as possible. In most of chemiluminescence measurement apparatuses that are commonly used today the nozzle and the photomultiplier tube are placed on the same stage, with the aims of high throughput, downsizing the apparatus, and cost reduction, as illustrated in Nonpatent Literature 1 (refer to FIG. 5 on page 11 thereof).

Moreover, Patent Literature 1 discloses a dispensing apparatus and an analysis apparatus equipped therewith described as: "a dispensing apparatus of the present invention comprises a dispensing tip 2, a syringe part 3, and a syringe base 4. The syringe part 3 includes a nozzle 11 extending in a vertical direction and having the dispensing tip 2 attached to its bottom end in the vertical direction. The syringe base 4 is provided with an elastic member 8 which supports the syringe part 3 movably and urges the syringe part 3 upward in the vertical direction. The syringe part 3 and the syringe base 4 are movable with respect to each other in the vertical direction."

CITATION LIST

Patent Literature

Patent Literature 1: Japanese Unexamined Patent Application Publication No. 2015-175707

Non Patent Literature

Nonpatent Literature 1: "Navigator System OPERATING MANUAL Instructions for Use of Products GM2000 and GM2010" (Online), GloMax, (Searched out on Dec. 28, 2018) Internet <URL: https://www.promega.jp/-/media/files/resources/protocols/technical-manuals/101/glomax-navigator-system-operating-manual.pdf?la=en>

SUMMARY OF INVENTION

Technical Problem

As described in Nonpatent Literature 1, when the nozzle and the photomultiplier tube are fixed on the same stage, "adjusting a height of the nozzle" and "adjusting a height of the photomultiplier tube" interlock with each other and the height of each part cannot be adjusted independently. As a result, dispensing and measurement cannot be performed except at a height designed in advance and a specification change of a microplate makes a design change needed.

Accordingly, a technology described in Nonpatent Literature 1 poses the following problems:

(A1) Redesign may be needed when the specifications of a microplate (such as depth) are changed;

(A2) Even if a contact of the nozzle with a specimen should not be allowed, a change in a liquid quantity (liquid level) of a specimen may cause the contact (A3) When a tip of the nozzle is positioned higher than a top surface of a plate, a luminescent reagent may spatter on the surface of the plate, when being dispensed.

(A4) When the photomultiplier tube floats from a well of a microplate, its sensitivity degrades and, besides, incident light from an adjacent well may induce luminous crosstalk.

(A5) When a measurement is performed for a well positioned at an end of a microplate under a condition of the tip of the nozzle being positioned lower than a photosensitive surface of the photomultiplier tube, the nozzle may hit against, for example, the top surface (deck) of an end portion of the microplate or the like when the photomultiplier tube moves down, which may contaminate the nozzle.

The present invention is developed in view of the technical background and the above-described problems, and it is an object of the invention to provide an apparatus performing an efficient luminescence measurement.

Solution to Problem

To solve the above-noted problem, the present invention provides an apparatus comprising: a nozzle for dispensing liquid into a well in a microplate, a luminescence measurement unit configured for measuring luminescence occurring in the well, and a moving unit configured for moving the nozzle and the luminescence measurement unit together vertically and horizontally, wherein the nozzle is secured to the moving unit, and the luminescence measurement unit is mounted to be vertically movable with respect to the moving unit.

Other solutions are described, as appropriately, in Description of Embodiments below.

Advantageous Effects of Invention

The present invention enables a more efficient luminescence measurement.

BRIEF DESCRIPTION OF DRAWINGS

FIG. 16 is a flowchart illustrating a procedure of a method for preventing dripping according to a third embodiment.

FIG. 18E is a diagram (step 5) explaining the procedure for dispensing the luminescent reagent and measuring the luminescence according to the fourth embodiment.

FIG. 18F is a diagram (step 6) explaining the procedure for dispensing the luminescent reagent and measuring the luminescence according to the fourth embodiment.

FIG. 18G is a diagram (step 7) explaining the procedure for dispensing the luminescent reagent and measuring the luminescence according to the fourth embodiment.

FIG. 18H is a diagram (step 8) explaining the procedure for dispensing the luminescent reagent and measuring the luminescence according to the fourth embodiment.

DESCRIPTION OF EMBODIMENTS

Next, embodiments for carrying out the present invention (referred to as simply "embodiments") are described in detail with reference to the drawings as appropriately as needed. Note that exaggeration, deformation, etc. are made in some of the figures and dimensions of each part in the figures are not always consistent with each other.

First Embodiment

<Chemiluminescence Measurement Apparatus 1>

Figure 1:
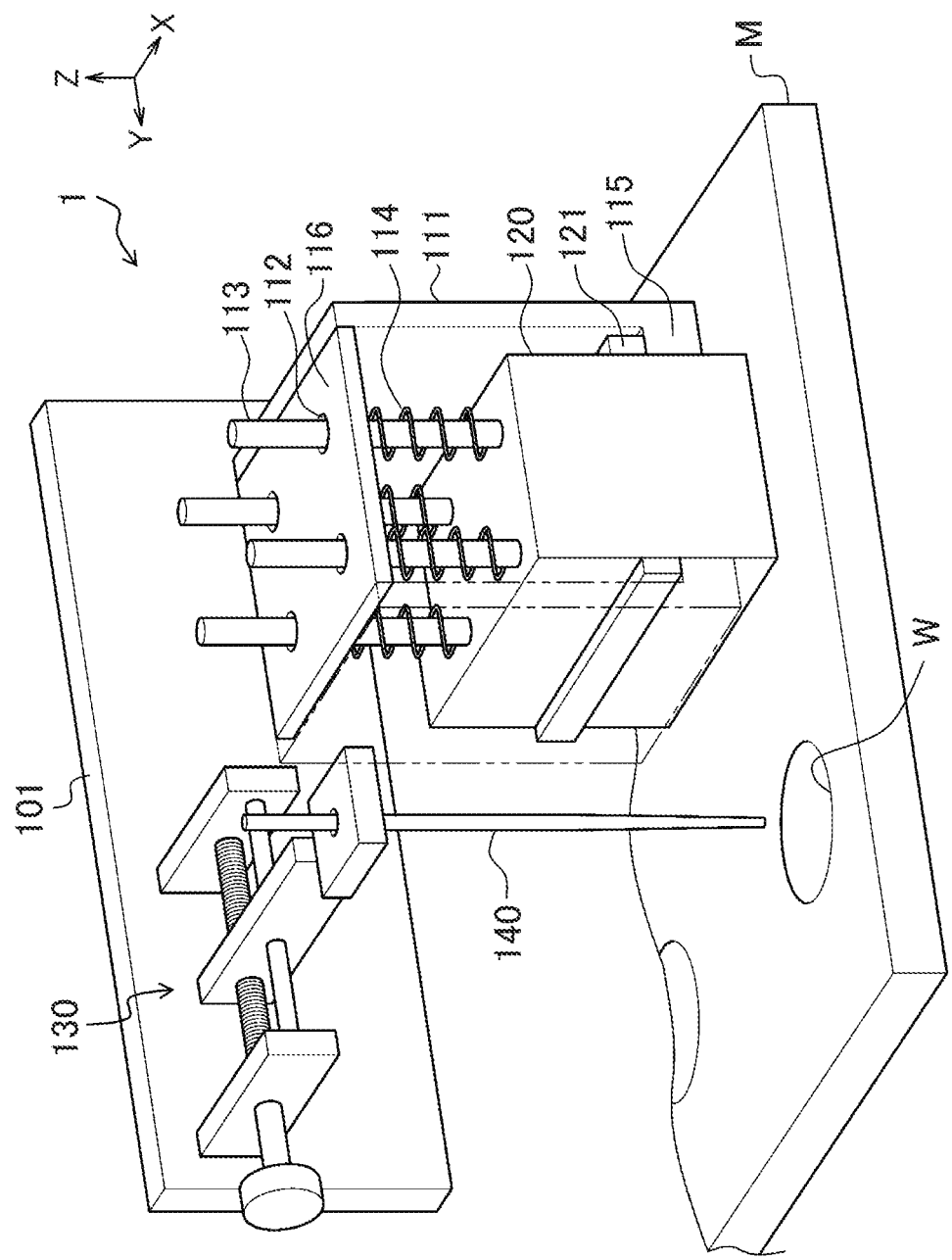
FIG. 1 is an external view of a chemiluminescence measurement apparatus according to a first embodiment.
Figure 2:
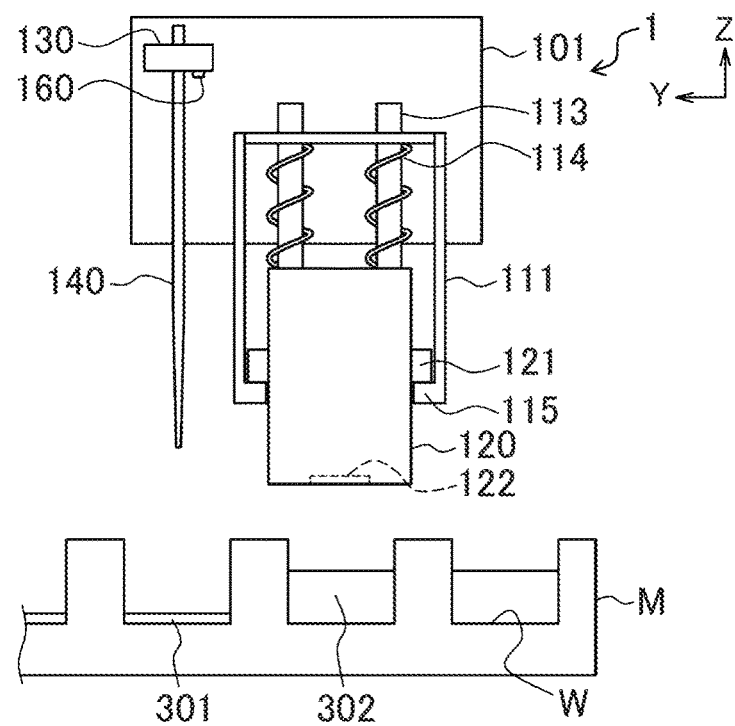
FIG. 2 is a front view of the chemiluminescence measurement apparatus.

FIG. 1 is an external view of a chemiluminescence measurement apparatus 1 according to a first embodiment. Additionally, FIG. 2 is a front view of the chemiluminescence measurement apparatus 1, when viewed in an X-axis direction in FIG. 1, and FIG. 3 is a side view of the chemiluminescence measurement apparatus 1, when viewed in a Y-axis direction in FIG. 1.

Figure 3:
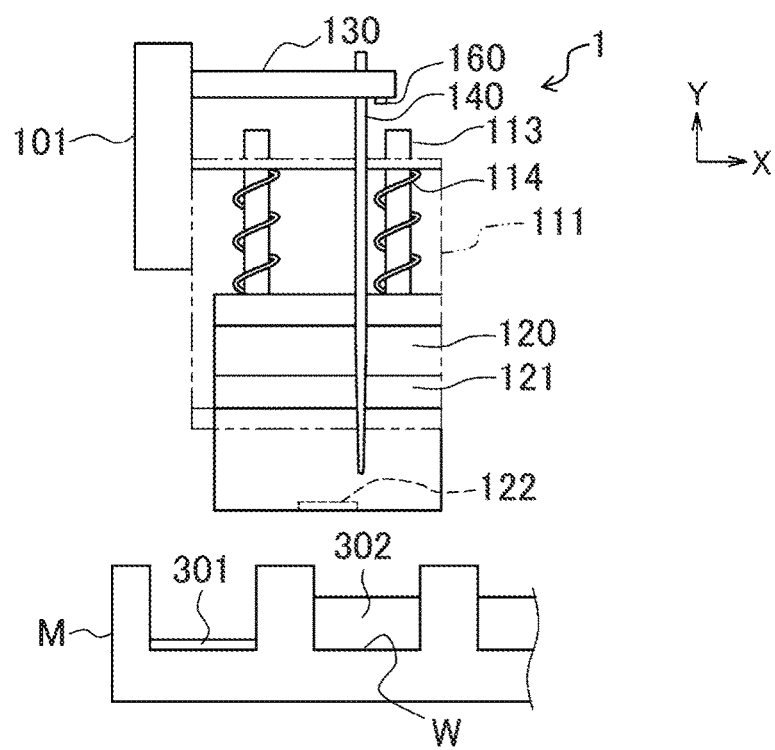
FIG. 3 is a side view of the chemiluminescence measurement apparatus.

As depicted in FIG. 1 and FIG. 3, the chemiluminescence measurement apparatus 1 has a stage (moving unit) 101 that moves in X-axis, Y-axis, and Z-axis directions in FIG. 1. A holder 111 is fixed to the stage 101. That is, the holder 111 is movable together with the stage 101 in the X-axis, Y-axis, and Z-axis directions. Hereinbelow, a positive direction along the Z axis in FIG. 1 is referred to as "up" and a negative direction along the Z axis "down".

As depicted in FIG. 1, a luminescence measurement unit 120 is housed inside the holder 111. The luminescence measurement unit 120 includes a photomultiplier tube (PMT) or the like.

In addition, as depicted in FIG. 1, holes 112 (four holes in an example in FIG. 1) are provided in a top board 116 of the holder 111 and supporting posts 113 are provided (inserted) through each of the holes 112 to penetrate the top board 116 of the holder 111. However, each supporting post 113 is not fixed with respect to the top board 116, but one end of each supporting post 113 is fixed to the luminescence measurement unit 120. Further, the bottom of the holder 111 is open so that a part of the luminescence measurement unit 120 is allowed to extend through the bottom surface of the holder 111.

Thereby, the luminescence measurement unit 120 is allowed to move vertically with respect to the holder 111 by being guided by the supporting posts 11 and the holes serving. Furthermore, each supporting post 113 is inserted through a spring 114. One end of the spring 114 is fixed to the luminescence measurement unit 120 and the other end is fixed to the top board 116 of the holder 111.

Additionally, the luminescence measurement unit 20 is provided at the bottom surface thereof with a photosensitive portion 122 to receive light emitted by a mixture liquid 302, as depicted in FIG. 2 and FIG. 3.

Further, pawls 115 are provided in the opening in the bottom surface of the holder 111. Also, first protrusions 121 are provided in lateral surfaces of the luminescence measurement unit 120. The first protrusions 121 of the luminescence measurement unit 120 are lathed by the pawls 115 so that the luminescence measurement unit 120 are prevented from falling from the holder 111 or can be avoided from extending from the holder 111 more than necessary.

The stage 101 is fixedly provided with a nozzle position adjusting part 130. The nozzle position adjusting part 130 is described below. The nozzle position adjusting part 130 is provide with a nozzle 140 to dispense a luminescent reagent (liquid) or the like into a well W of the microplate M. That is, the stage 101 is provided with the nozzle 140 via the nozzle position adjusting part 130. Because the nozzle position adjusting part 130 is fixed to the stage 101, the nozzle 140 moves accompanying with movement of the stage 101. Note that the nozzle 140 is essential, but the nozzle position adjusting part 130 may be dispensed with.

The nozzle 140 is connected to a syringe which is not depicted. The syringe is controlled to regulate the discharge of the luminescent reagent through the nozzle 140.

Also, as depicted in FIG. 2 and FIG. 3, the nozzle position adjusting part 130 is provided with a nozzle position sensor (detector) 160. The nozzle position sensor 160 is a sensor to detect a distance between the nozzle 140 and the microplate M. Herein, the nozzle position sensor 160 is assumed to be a laser distance sensor or the like, but it is also possible to make the nozzle 140 itself the nozzle position sensor 160 by making the nozzle 140 itself serve as a capacitance sensor. In the case of making the nozzle 140 itself serve as the capacitance sensor, the nozzle 140 should preferably be configured with two metal members and a rubber member connecting these metal members. In the nozzle thus configured, the two metal members function as two electrodes of the capacitance sensor. In a case where the stage 101 is moved down until the nozzle 140 contacts to a specimen 301, the nozzle 140 itself should preferably be made to serve as the nozzle position sensor 160 by making the nozzle 140 itself serve as the capacitance sensor.

<System>

Figure 4:
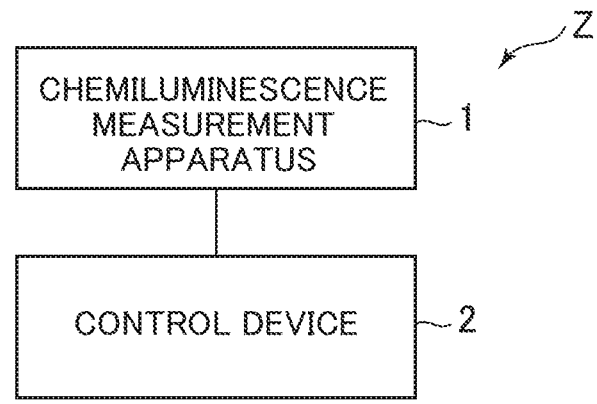
FIG. 4 is a diagram depicting a configuration of a chemiluminescence measurement system according to the first embodiment.

FIG. 4 is a diagram depicting a configuration of a chemiluminescence measurement system Z according to the first embodiment.

The chemiluminescence measurement system Z includes the chemiluminescence measurement apparatus 1 described with FIGS. 1 through 3. and a control device 2 that connects with the chemiluminescence measurement apparatus 1 and controls the chemiluminescence measurement apparatus 1. The chemiluminescence measurement apparatus 1 and the control device 2 may be wired or wirelessly connected. Also, the chemiluminescence measurement apparatus 1 and the control device 2 may be connected via a LAN (Local Area Network). Alternatively, the control device 2 may remotely control the chemiluminescence measurement apparatus 1 via a WAN (Wide Area Network) or the like.

<Control Device 2>

Figure 5:
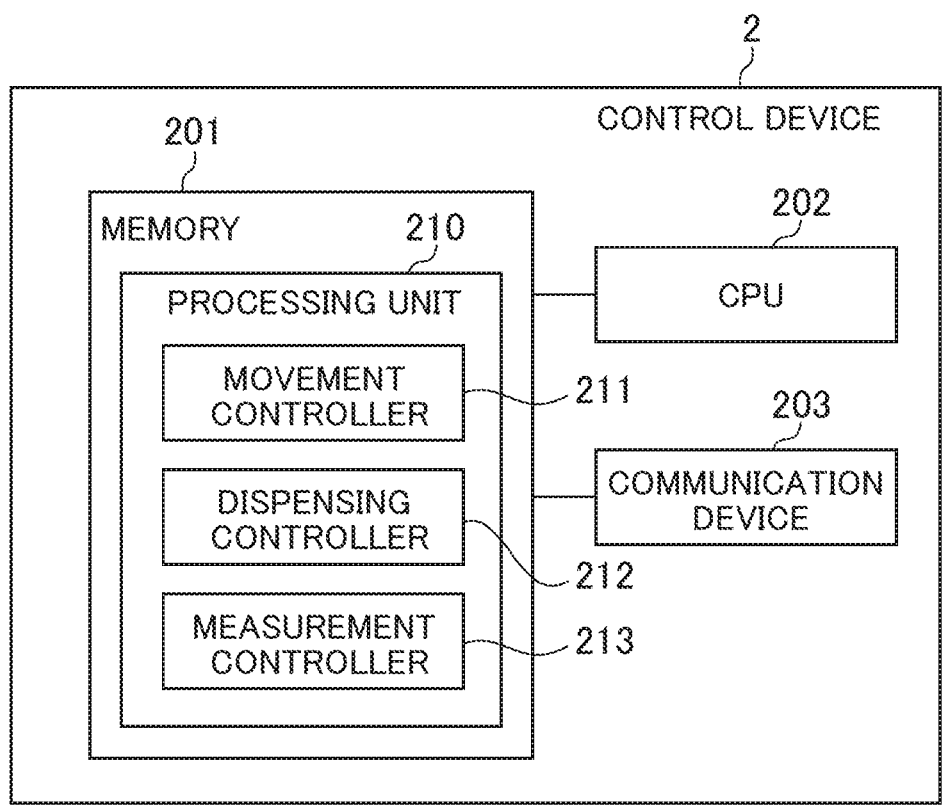
FIG. 5 is a diagram depicting a configuration of a control device used in the first embodiment.

FIG. 5 is a diagram depicting a configuration of the control device 2 used in the first embodiment. A description is made with reference to FIG. 1, appropriately as needed.

The control device (control unit) 2 may be a PC (Personal Computer), a PLC (programmable Logic Controller) or the like, and includes a memory 201, a CPU 202, and a communication device 203 for communicating with the chemiluminescence measurement apparatus 1.

The memory 201 includes a program stored in and loaded from a storage device which is not depicted. The loaded programs are then executed by the CPU 202 and, thereby, a processing unit 201 and a movement controller 211, a dispensing controller 212, and a measurement controller 213 which are included in the processing unit 201 are embodied.

The movement controller 211 controls movement of the stage 101.

The dispensing controller 212 controls the syringe (not depicted) to dispense a luminescent reagent or the like.

The measurement controller 213 controls luminescence measurement performed by the luminescence measurement unit 120.

<Operation of the Chemiluminescence Measurement Apparatus 1>

Next, with reference to FIGS. 6 through 9, operation of the chemiluminescence measurement apparatus 1 is described, with reference to FIG. 5, appropriately as needed.

Here is assumed that the chemiluminescence measurement apparatus 1 is in a state that a specimen 301 has been dispensed in wells W of the microplate M and a mixture liquid 302 is produced by dispensing a luminescent reagent from the nozzle 140 into the specimen 301. The specimen 301 may be dispensed by either human or through the nozzle 140. If the specimen 301 is dispensed by the nozzle 140, the nozzle 140 is replaced after dispensing the specimen 301. Here, when a luminescent reagent is dispensed into the specimen 301, chemical reaction of the specimen 301 with the luminescent reagent makes the mixture liquid 302 produce luminescence. Measuring an amount of such luminescence enables the luminescence measurement unit 120 to measure a quantity of an intended substance.

Figure 6:
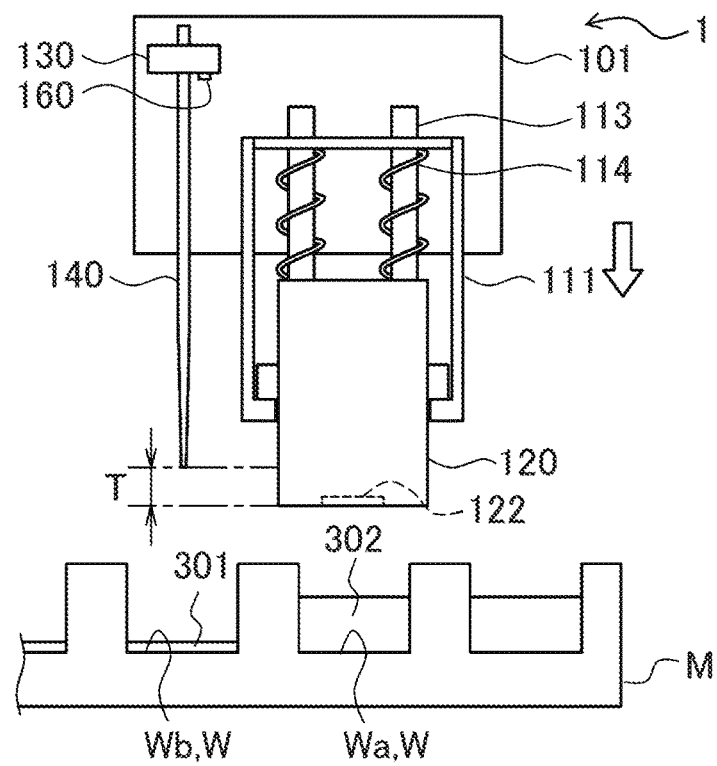
FIG. 6 is a diagram (step 1) explaining operation of the chemiluminescence measurement apparatus.

In FIG. 6, in a well Wb of the microplate M, only the specimen 301 is dispensed and a luminescent reagent is going to be dispensed by the nozzle 140. Further, in a well Wa, the luminescent reagent is completed to be dispensed into the specimen 301 and luminescence produced by the mixture liquid 302 is going to be measured by the luminescence measurement unit 120.

First, as depicted in FIG. 6, the movement controller 211 horizontally moves the stage 101 to position the nozzle 140 just above the well Wb and the luminescence measurement unit 120 just above the well Wa. At this time, it could be understood that before the nozzle 140 and the luminescence measurement unit 120 are set over the microplate M, a bottom end of the nozzle 140 is positioned higher by a distance of T than a bottom end of the luminescence measurement unit 120. Thus, the luminescence measurement unit 120 contacts the microplate M before the nozzle 140 does. This allows to prevent the tip of the nozzle 140 from being damaged, because the nozzle 140 is fixed to the stage 101.

Next, the movement controller 211 moves the stage 101 down, as indicated by a blank arrow in FIG. 6.

Figure 7:
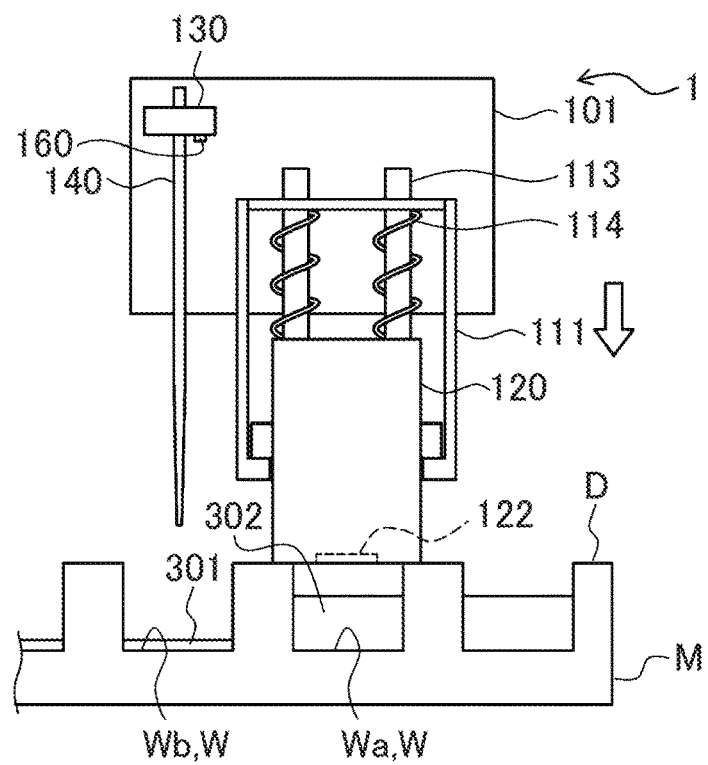
FIG. 7 is a diagram (step 2) explaining the operation of the chemiluminescence measurement apparatus.

Then, the luminescence measurement unit 120 contacts a deck D of the microplate M, as depicted in FIG. 7. After this, the movement controller 211 moves the stage 101 down farther, as indicated by a blank arrow in FIG. 7.

Figure 8:
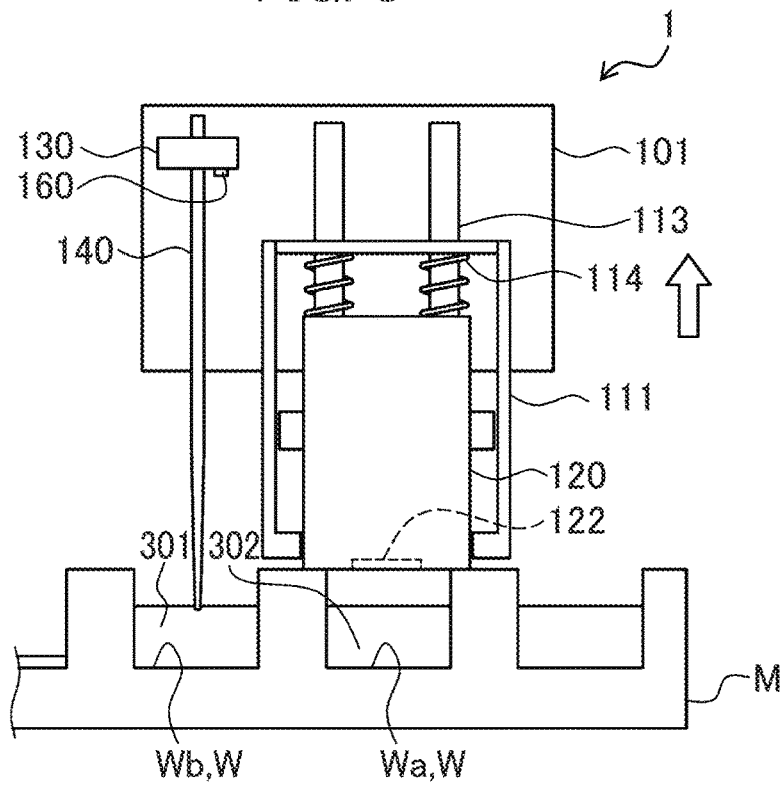
FIG. 8 is a diagram (step 3) explaining the operation of the chemiluminescence measurement apparatus.

This results in shrinking of the springs 114 through which the supporting posts 113 are inserted, as depicted in FIG. 8. Furthermore, the movement controller 211 moves the stage 101 down to a predetermined (desired) height of the nozzle 140 for dispensing the luminescent reagent. Whether or not the nozzle 140 is at a height suitable for dispensing the luminescent reagent is detected by the nozzle position sensor 160. Note that the "height suitable for dispensing" is preset by a user.

Then, the dispensing controller 212 makes the nozzle 140 to dispense the luminescent reagent into the well Wb. This results in a mixture liquid 302 in the well Wb. Also, at the same time of dispensing the luminescent reagent by the nozzle 140, luminescence produced by the mixture liquid 302 in the well Wa is measured by the luminescence measurement unit 120.

When the dispensing and the measurement are finished, the movement controller 211 moves the stage 101 upward, as indicated by a blank arrow in FIG. 8. This allows the nozzle 140 and luminescence measurement unit 120 to move upward, while allowing the shrunk springs 114 to recover gradually.

Figure 9:
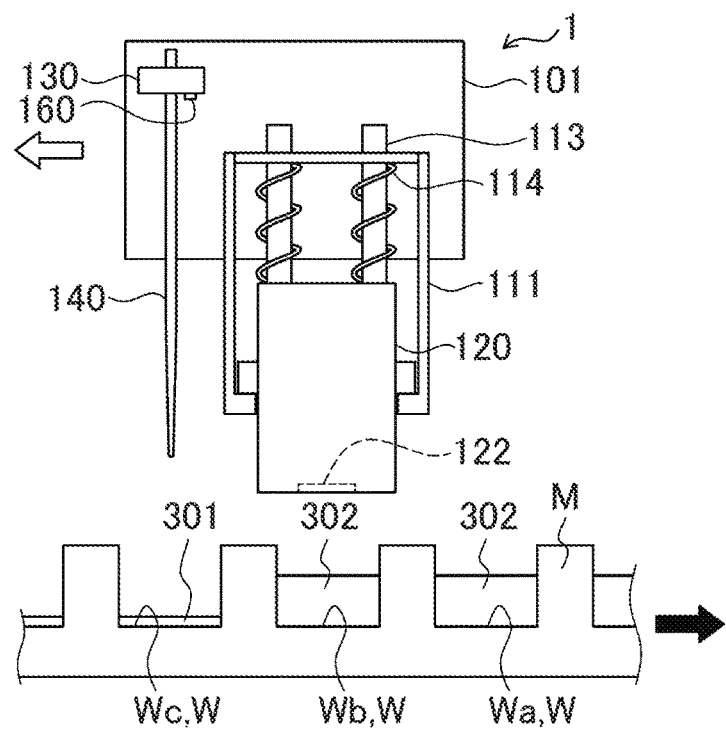
FIG. 9 is a diagram (step 4) explaining the operation of the chemiluminescence measurement apparatus.

When the nozzle 140 and the luminescence measurement unit 120 move up to the previous position before they are set over the respective wells W, the movement controller 211 horizontally moves the stage 101, as indicated by a blank arrow in FIG. 9.

That is, the movement controller 211 horizontally moves the stage 101 to position the luminescence measurement unit 120 just above the well Wb into which the luminescent reagent is dispensed by the nozzle 140 and the nozzle 140 just above the well Wc into which the luminescent reagent is dispensed next.

Further, the microplate M is horizontally moved in a direction indicated by a bold arrow in FIG. 9 (a direction opposite to the direction in which the stage 101 horizontally moves) by a microplate moving unit which is not depicted. The horizontal movement of the microplate M is performed concurrently with the horizontal movement of the stage 101. This enables time for moving the stage 101 to be shortened and throughput to be improved. As described above, the microplate M moves only in a horizontal direction. At the same time as the horizontal movement of the stage 101, the microplate M horizontally moves in the direction opposite to the direction in which the stage 101 horizontally moves; however, the direction in which the microplate M moves is omitted from the drawings after FIG. 9 to prevent the drawings from becoming complicated.

Subsequently, by repeating the operation illustrated in FIGS. 6 through 8, the luminescent reagent is dispensed into the well Wc and luminescence produced by the mixture liquid 302 in the well Wb is measured, as illustrated in FIG. 8.

Note that an interval between the nozzle 140 and the luminescence measurement unit 120 is adjusted beforehand by the nozzle position adjusting part 130 so as to be equal to an interval between wells W.

<Flowchart>

Figure 10:
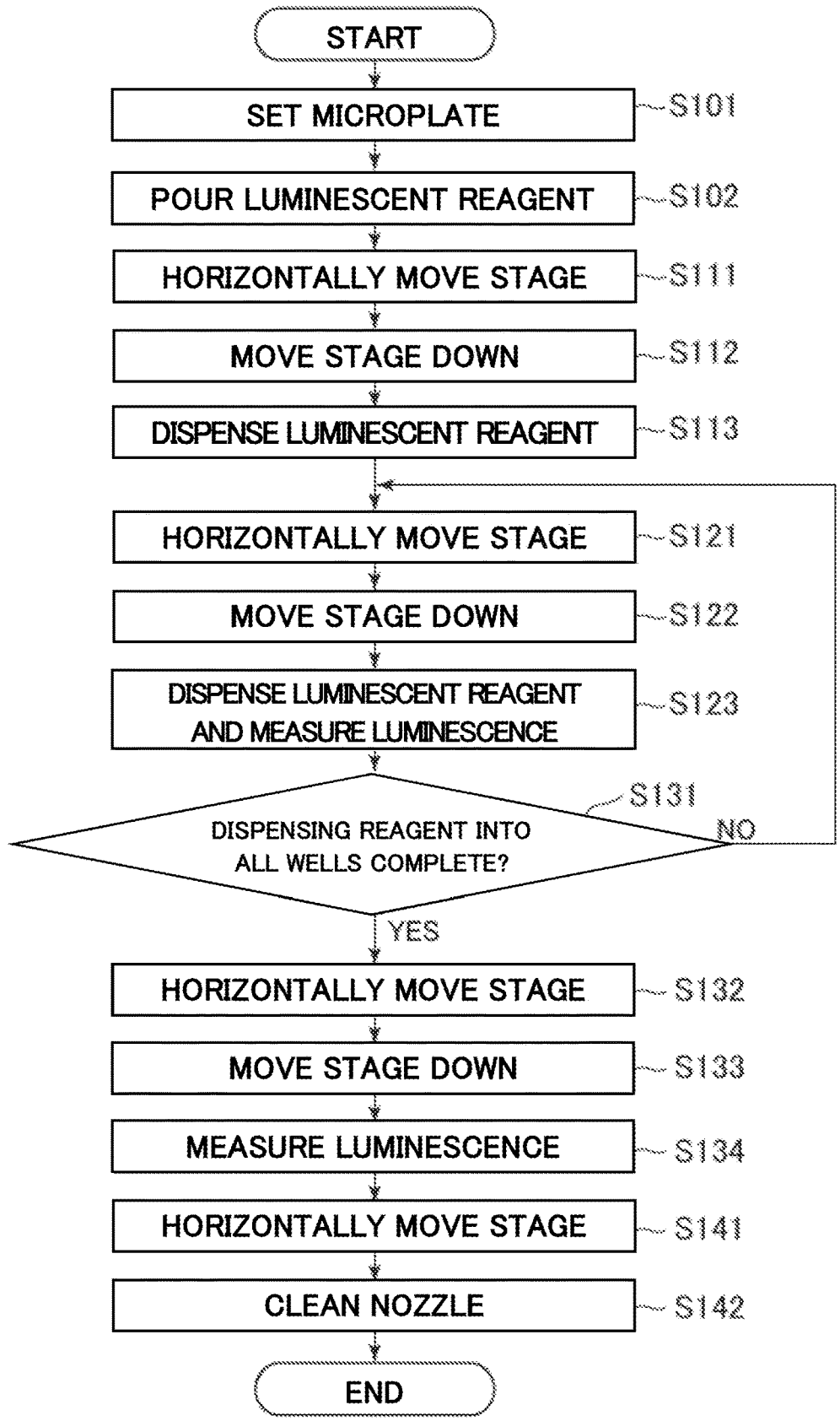
FIG. 10 is a flowchart illustrating a processing procedure that is performed by the control device according to the first embodiment.

FIG. 10 is a flowchart illustrating a processing procedure that is performed by the control device 2 in the first embodiment.

First, a user sets the microplate M with the specimen 301 dispensed (S101). Further, the user pours a luminescent reagent into a cylinder (not depicted) which is connected to the nozzle 140 (S102). Furthermore, the user performs a horizontal position adjustment of the nozzle 140 using the nozzle position adjusting part 130, if necessary.

Next, the movement controller 211 horizontally moves the stage 101 to position the nozzle 140 just above the well W into which the luminescent reagent is first dispensed (S111).

Then, the movement controller 211 moves the stage 101 down to a position appropriate for dispensing (S112). The nozzle position sensor 160 detects whether or not the position is appropriate. It should be noted that an appropriate position differs depending on measurement conditions. Thus, detecting whether or not the position is appropriate by the nozzle position sensor 160 allows adjustment by the user to be unnecessary and to improve throughput.

Subsequently, the dispensing controller 212 causes the nozzle 140 to dispense the luminescent reagent (S113). Note that because there is no well W for which luminescence measurement can be performed at the stage of step S113, luminescence measurement is not performed.

When the dispensing finishes, the movement controller 211 horizontally moves the stage 101 (S121). Here, after moving the stage 101 up, the movement controller 211 horizontally moves the stage 101 to position the nozzle 140 just above the well W into which the luminescent reagent is to be dispensed next and position the luminescence measurement unit 120 just above the well W into which the luminescent reagent is dispensed.

Next, the movement controller 211 moves the stage 101 down (S122; FIG. 6 and FIG. 7). After a short while, when the nozzle 140 is moved down to a position appropriate for dispensing the luminescent reagent, the dispensing controller 212 causes the nozzle 140 to dispense the luminescent reagent and the luminescence measurement unit 120 to perform luminescence measurement (S123; FIG. 8). Note that here is started with dispensing the luminescent reagent by the nozzle 140 and luminescence measurement by the luminescence measurement unit 120 at the same time; the embodiment is, however, not limited thereto. For example, as illustrated in FIG. 7, while the nozzle 140 is not yet moved down to a position appropriate for dispensing, the luminescence measurement unit 120 may shut a target well for luminescence measurement and begin luminescence measurement. It is essential that the luminescence measurement by the luminescence measurement unit 120 should be performed while the luminescence measurement unit 120 shuts a target well W for luminescence measurement, as depicted in FIG. 7 and FIG. 8.

When the dispensing and luminescence measurement finish, the movement controller 211 moves the stage 101 up until the nozzle 140 and the luminescence measurement unit 120 arrive at the position before they are set over the respective wells W (FIG. 8).

After that, the dispensing controller 212 determines whether dispensing the reagent into all wells is complete or not (S131).

As a result of step S131, if it is determined that dispensing the reagent into all the wells is not complete (S131→No), the processing unit 210 causes the process to return to the step S121.

As a result of the step S131, if it is determined that dispensing the reagent into all the wells is complete (S131→Yes), the movement controller 211 horizontally moves the stage 101 to position the luminescence measurement unit 120 just above the last well W into which the luminescent reagent is dispensed (S132).

Then, the movement controller 211 moves the stage 101 down (S133).

When moving down the stage 101 finishes, the measurement controller 213 causes the luminescence measurement unit 120 to perform luminescence measurement (S134). Here, the finish of moving down of the stage 101 is determined by the position of the nozzle 140, which position is detected by the nozzle position sensor 160. Besides, because there is no well into which the reagent is to be dispensed in the step S134, luminescence measurement only is performed.

Note that here is assumed that dispending and luminescence measurement are performed for wells forming a single line; the steps S111 through S134 may be, however, repeated for wells W in all lines formed on the microplate M.

Then, the movement controller 211 horizontally moves the stage 101 (S141). Here, the movement controller 211 horizontally moves the stage 101 so that the nozzle 140 arrives at a nozzle cleaning part which is not depicted.

After that, cleaning the nozzle 140 by the nozzle cleaning part, not depicted, is performed (S142).

<Nozzle Position Adjusting Part 130>

Figure 11:
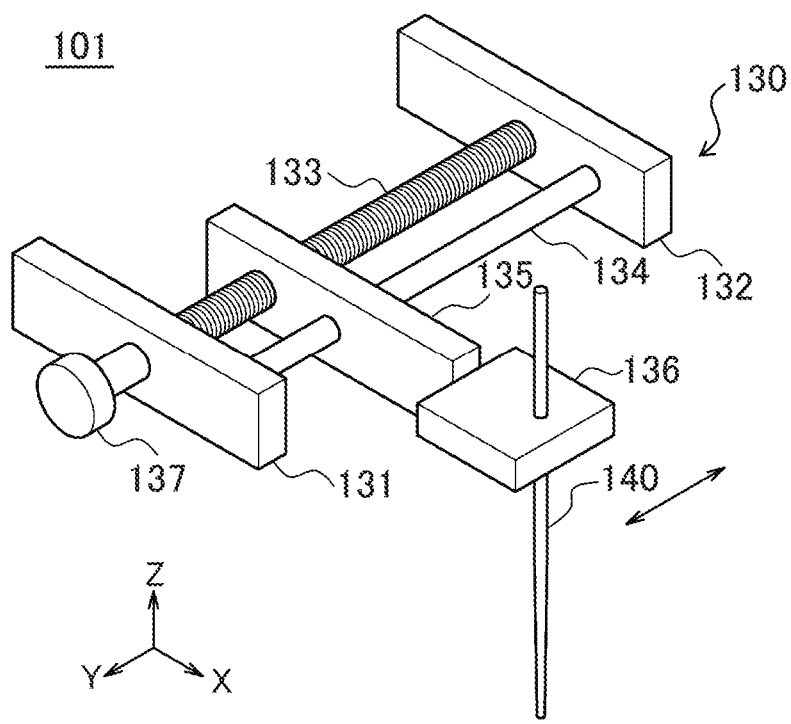
FIG. 11 is an enlarged view of a nozzle position adjusting part.

FIG. 11 is an enlarged view of the nozzle position adjusting part 130. The nozzle position adjusting part 130 includes a first support 131 and a second support 132 which are fixed to the stage 101. The first support 131 and second support 132 are connected with each other by a feed screw 133 and a bar-like guide 134. Also, the feed screw 133 and the guide 134 are inserted through a first nozzle support 135, as depicted in FIG. 11. Note that the first nozzle support 135 is not fixed to the guide 135. That is, the first nozzle support 135 is movable with respect to the guide 134.

Additionally, the first nozzle support 135 has its front-end face fixed with a second nozzle support 136. And, the nozzle 140 is inserted through the second nozzle support 136 so that the nozzle 140 is secured to the nozzle position adjusting part 130.

Also, the first support 131 is provided with a knob 137 at its reverse side of a side opposite to the second support 132. The knob 137 is connected to the feed screw 133.

When the user turns the knob 137, the feed screw 133 rotates. With the rotation of the feed screw 133, the first nozzle support 135 moves horizontally (in the y-axis direction). With movement of the first nozzle support 135, the second nozzle support 136 moves and, thereby, the nozzle 140 moves horizontally (in the y-axis direction). This means that the nozzle position adjusting part 130 is operated by hand.

Note that the structure of the nozzle position adjusting part 130 depicted in FIG. 11 is an example and any structure may be allowable, in which structure the horizontal position (position in the y-axis direction) of the nozzle can be adjusted by hand.

Besides, the nozzle position adjusting part 130 may be a linear actuator that can move linearly in the y-axis direction. In this case, the linear actuator may be moved according to a command entered via an input device, which is not depicted, of the control device 2 to adjust the horizontal position of the nozzle 140.

Figure 12:
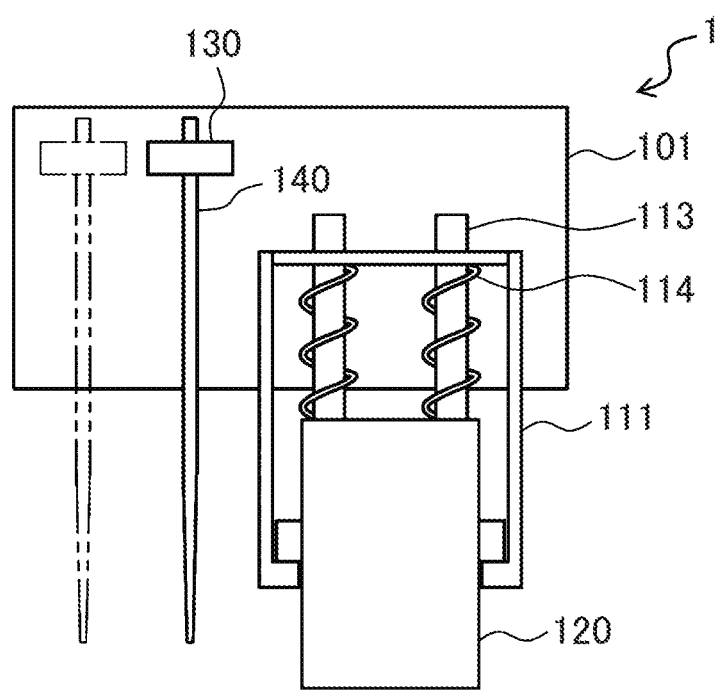
FIG. 12 is a diagram depicting position adjustment of the nozzle by the nozzle position adjusting part.

FIG. 12 is a diagram depicting position adjustment of the nozzle 140 by the nozzle position adjusting part 130.

As depicted in FIG. 12, the horizontal position (position in the y-axis direction in FIG. 1) of the nozzle 140 with respect to the luminescence measurement unit 120 can be changed by the nozzle position adjusting part 130.

As noted above, a pitch between wells W in the microplate M depends on specifications, manufacturers, and the like. Because the horizontal position of the nozzle 140 can be adjusted by the provision of the nozzle position adjusting part 130, it is possible to make an interval between the luminescence measurement unit 120 and the nozzle 140 keep a pitch between wells W. That is, it is possible to readily respond to a specification change of the pitch between the wells W.

As described above, the provision of the nozzle position adjusting part 130 allows to easily make the positional relation between the nozzle 140 and the luminescence measurement unit 120 equal to an interval between wells in the microplate M. Thus, it is possible to easily perform a dispensing operation into a next well W, while performing the luminescence measurement by the luminescence measurement unit 120. This results in the improvement in the throughput.

According to the first embodiment, the luminescence measurement unit 120 is mounted to be movable vertically from/to the holder 111 (stage 101), as in FIG. 1, and, thereby, the luminescence measurement unit 120 can be pressed against the surface of the microplate M. This allows to diminish crosstalk attributed to luminescence occurring in an adjacent well W. Also, the springs 114 serve as a cushion so that the luminescence measurement unit 120 may be prevented from being damaged by an accident of contacting with the microplate M.

Second Embodiment

Figure 13:
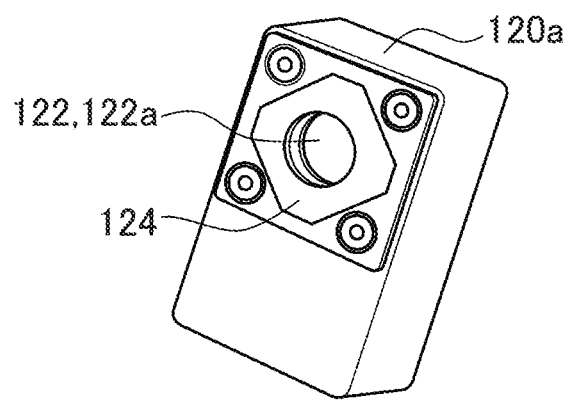
FIG. 13 is a view of a luminescence measurement unit according to a second embodiment, when viewed from a photosensitive portion.
Figure 14:
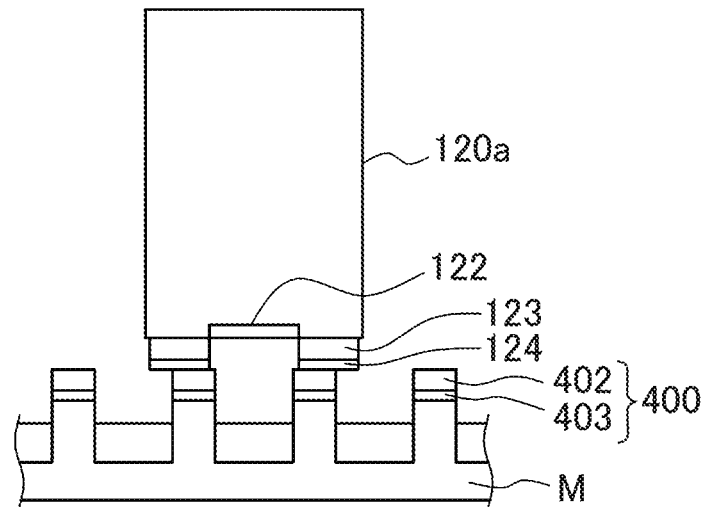
FIG. 14 is a cross-sectional view of a microplate and the luminescence measurement unit in a state of the luminescence measurement unit being set on a plate mask attached onto the microplate.
Figure 15:
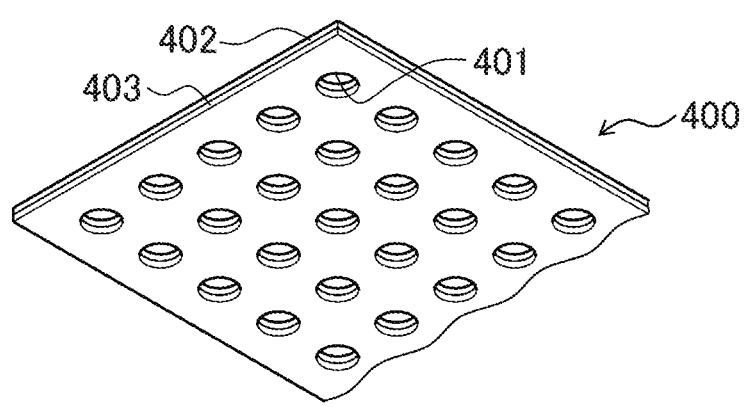
FIG. 15 is a view of the plate mask according to the second embodiment, when viewed from below.

FIGS. 13 through 15 are diagrams depicting a plate mask 400 and a luminescence measurement unit 120a in a second embodiment. FIG. 13 is a view of the luminescence measurement unit 120a in the second embodiment, when viewed from a side of the photosensitive portion 122. FIG. 14 is a cross-sectional view of a state in which a plate mask 400 is attached onto a microplate M and the luminescence measurement unit 120a is set on the plate mask 400. Furthermore, FIG. 15 is a view of the plate mask 400 according to the second embodiment, when viewed from below.

The luminescence measurement unit 120a, as depicted in FIG. 13 and FIG. 14, is provided with a metal portion 123 and a rubber portion (cushion portion) 124 around a photosensitive surface 129a where the photosensitive portion 122 is exposed. Here, the metal portion 123 and the rubber portion 124 are provided in an order from the metal portion 123 to the rubber portion 124, starting from the side of the luminescence measurement unit 120a, as depicted in FIG. 14. However, a structure between the luminescence measurement unit 120a and the rubber portion 124 may be made of any kind of member, as long as a part contacting the microplate M is made of the rubber portion 124. For example, the metal part 123 may be omitted and the rubber portion 124 may be directly attached to the luminescence measurement unit 120a.

The structure provided as above allows to press the luminescence measurement unit 120a more tightly against the microplate M than in the first embodiment. Such a structure may improve adhesion between the microplate M and the luminescence measurement unit 120a and prevent a crosstalk caused by light from an adjacent well.

Moreover, the chemiluminescence measurement apparatus 1 is provided with the plate mask 400 as depicted in FIG. 15. As depicted in FIG. 15, the plate mask 400 includes a metal portion 402 and a rubber portion (cushion portion) 403 which have a flat plate shape, and is provided with holes 401 penetrating the metal portion 402 and the rubber portion 403 and allowing the nozzle 140 to insert therethrough. Further, the plate mask 400 is placed onto the microplate M to be used and includes the rubber portion 403 and the metal portion 402 in the immediately aforementioned order starting from the side of the microplate M, as depicted in FIG. 14 and FIG. 15, here is only required that a portion contacting the microplate M is made of the rubber portion 403. Furthermore, a surface of the metal portion 402 which is attached with none of the rubber portion 403 is flat. It should be noted that a surface of the rubber portion 403 (its side contacting the microplate M) should preferably be flat, although it is not mandatory.

Microplates M have minute unevenness that differs depending on standard specifications and manufacturers. Consequently, some of the microplates M poses a problem that adhesion may be deteriorated when pressing the photosensitive surface of the photosensitive portion against the microplate M. The deterioration of adhesion brings about a problem of a crosstalk caused by the light from the well W adjacent to the target well for luminescence measurement.

To cope with such a problem, in the second embodiment, the microplate M is placed thereon with the plate mask 400 having the rubber portion 403 contacting the microplate M. Thus, the rubber portion 403 contacting the microplate M absorbs the difference in unevenness of the microplate M. Moreover, a surface of the metal portion 402 not provided with the rubber portion (the surface abutting the luminescence measurement unit 120) is flat. By placing such a plate mask 400 onto the microplate M, the surface that the luminescence measurement unit 120*a* contacts can be flat. Moreover, the soft rubber portion 403 allows to improve adhesion when the luminescence measurement unit 120*a* is pressed against the microplate. Then, this improvement of adhesion allows to prevent the crosstalk caused by the light from the well W adjacent to the target well for luminescence measurement.

Furthermore, use of the luminescence measurement unit 120*a* provided with the rubber portion 124 around the photosensitive portion 122 together with the plate mask 400 can prevent crosstalk.

Alternatively, use of only the luminescence measurement unit 120*a* provided with the rubber portion around the photosensitive portion 122 without using the plate mask 400 can also prevent crosstalk.

Third Embodiment

When dispensing a fixed quantity of a luminescent reagent continuously and at high speed, dripping from the tip of the nozzle 140 becomes a problem. Occurrence of dripping poses a problem that an accurate liquid volume cannot be dispensed. Also, there is a problem that a dripped sample and/or luminescent reagent remaining on the deck D (see FIG. 7) of the microplate M may contaminate the luminescence measurement unit 120. To solve such problems, the third embodiment proposes a method for preventing the dripping as described below.

FIG. 16 is a flowchart illustrating a procedure of the method for preventing the dripping in the third embodiment. FIGS. 17A through 17D are diagrams depicting the procedure of the method for preventing the dripping.

In the following, reference is made to FIG. 16 and also to FIGS. 17A through 17D, as appropriately as needed.

Figure 17A:
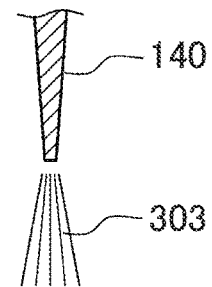
FIG. 17A is a diagram (step 1) depicting the procedure of the method for preventing dripping.

First, before dispensing a reagent into wells W, the dispensing controller 212 causes the nozzle 140 to eject a luminescent reagent 303 (S201; see FIG. 17A).

Figure 17B:
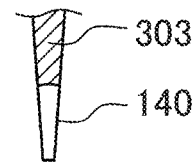
FIG. 17B is a diagram (step 2) depicting the procedure of the method for preventing dripping.
Figure 17C:
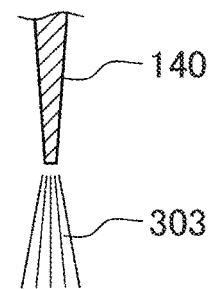
FIG. 17C is a diagram (step 3) depicting the procedure of the method for preventing dripping.

Next, after completion of ejecting the luminescent reagent 303, the dispensing controller 212 controls the cylinder (not depicted) to suck in air as much as a liquid volume q from the nozzle 140 (S202). This causes an interior of the nozzle 140 to be filled with air from the tip to a level to suck in as much as the liquid volume q, as depicted in FIG. 17B. This state of the nozzle allows to prevent dripping through the tip of the nozzle 140.

Then, moving the stage 101 horizontally and downward (S21) are performed by the movement controller 211 to position the nozzle 140 just above a well into which the luminescent reagent 303 is dispensed first. This process corresponds to the process of the steps S111, S112, S121, and S122 in FIG. 10.

Next, the dispensing controller 212 performs dispensing the luminescent reagent 303 into the well W (S212). This process corresponds to the step S113 or step S123 in FIG. 10. At this time, when it is desired to dispense the luminescent reagent 303 of a liquid volume Q into the well W, the dispensing controller 212 controls the cylinder (not depicted) to dispense the luminescent reagent 303 of a liquid volume Q+q. As described previously, because the nozzle 140 is in the state in which its interior is filled with air from the tip thereof to the level of as much as the liquid volume q, the cylinder is controlled to dispense the luminescent reagent 303 of the liquid volume Q+q. Thus, the luminescent reagent 303 of the desired liquid volume is dispensed.

Figure 17D:
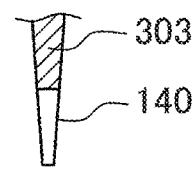
FIG. 17D is a diagram (step 4) depicting the procedure of the method for preventing dripping.

When dispensing finishes, the dispensing controller 212 controls the cylinder (not depicted) to suck in air as much as the liquid volume q through the nozzle 140 (S213). This causes an interior of the nozzle 140 to be filled with air from the tip to the level of as much as the liquid volume q, as depicted in FIG. 17D. This state of the nozzle 140 allows to prevent dripping through the tip of the nozzle 140.

Subsequently, the processing unit 210 repeats steps S211 through 213 until dispensing finishes.

In the third embodiment, sucking in air as much as the liquid volume q is done beforehand and the dispensing controller 212 performs the dispensing the luminescent reagent 303 of a liquid volume Q desired to be dispensed+ vacant liquid volume q. After dispensing, air as much as the liquid volume q is sucked in to prevent dripping. Thus, dripping can be prevented, and an accurate liquid volume can be dispensed.

Fourth Embodiment

Next, a description is given of a procedure for dispensing the luminescent reagent 303 and performing the luminescence measurement in a fourth embodiment with reference to FIGS. 18A through 18H.

Figure 18A:
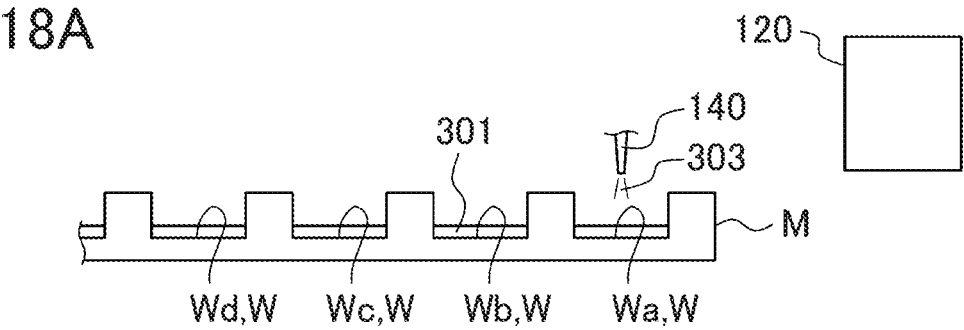
FIG. 18A is a diagram (step 1) explaining a procedure for dispensing a luminescent reagent and measuring luminescence according to a fourth embodiment.

(B1) First, dispensing the luminescent reagent 303 into the well Wa is performed by the nozzle 140, as depicted in FIG. 18A. At this time, luminescence measurement by the luminescence measurement unit 120 is not performed.

Figure 18B:
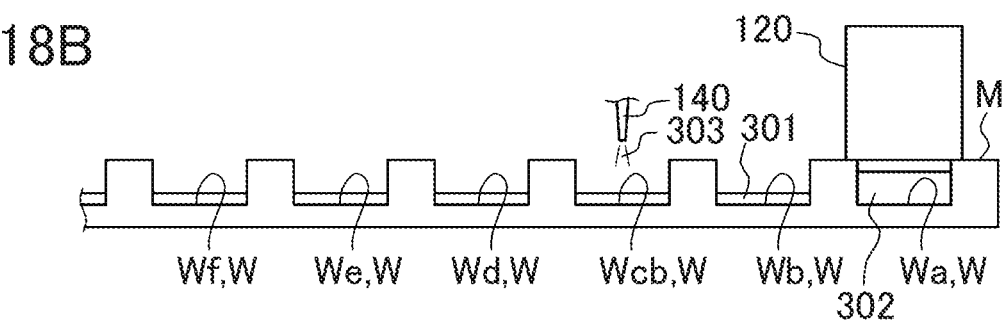
FIG. 18B is a diagram (step 2) explaining the procedure for dispensing the luminescent reagent and measuring the luminescence according to the fourth embodiment.

(B2) Next, horizontally moving the stage 101 is performed by the movement controller 211. At this time, the stage 101 is horizontally moved above the well Wc skipping the well Wb adjacent to the well Wa into which the reagent is already dispensed at (B1) so that dispensing the reagent into the well Wc may be performed. That is, dispensing the luminescent reagent 303 into the well Wc is performed by the nozzle 140, as depicted in FIG. 18B, and, at the same time, a measurement is performed for luminescence produced by mixture liquid 302 in the well Wa into which the reagent is dispensed at (B1).

Figure 18C:
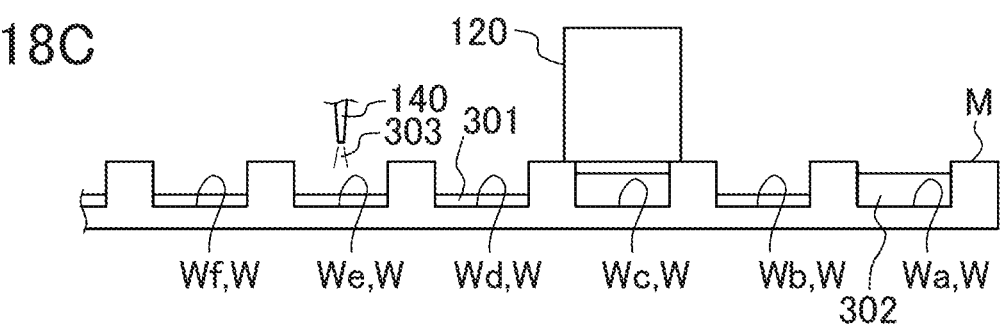
FIG. 18C is a diagram (step 3) explaining the procedure for dispensing the luminescent reagent and measuring the luminescence according to the fourth embodiment.

(B3) Then, horizontally moving the stage 101 is performed by the movement controller 211. At this time, the stage 101 is horizontally moved skipping a well Wd adjacent to the well Wd into which the reagent was dispensed in (B2) so that dispensing the reagent into a well We is performed. That is, dispensing the luminescent reagent 303 into the well We is performed through the nozzle 140, as depicted in FIG. 18C, and, at the same time, a measurement is performed of luminescence produced by the mixture liquid 302 in the well Wc into which the reagent is dispensed at (B2).

Figure 18D:
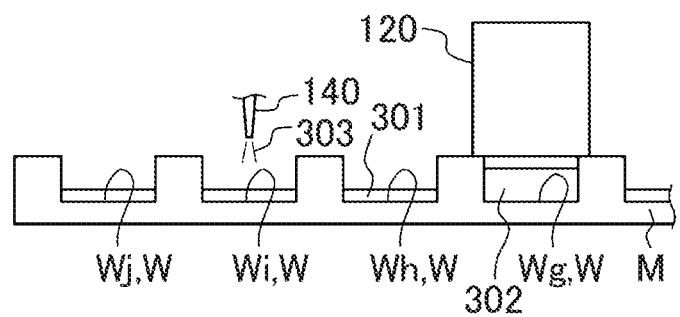
FIG. 18D is a diagram (step 4) explaining the procedure for dispensing the luminescent reagent and measuring the luminescence according to the fourth embodiment.

(B4) After several steps, dispensing the reagent into a well Wi located at a terminal side of the microplate M is performed through the nozzle 140, as depicted in FIG. 18D, and a measurement is performed by the luminescence measurement unit 120 of luminescence in a well Wg into which the reagent is dispensed preceding the well Wi.

(B5) After that, a measurement is performed of luminescence produced by the mixture liquid 302 in the well Wi into which the reagent is dispensed at (B4). At this time, dispensing through the nozzle 140 is not performed.

(B6) Then, the movement controller 211 returns the nozzle 140 and the luminescence measurement unit 120 to a starting side of the microplate M. At this time, the stage 101 is horizontally moved to perform dispensing the reagent into the well Wb which is located near the starting side of the microplate M and into which the reagent is not yet dispensed, as depicted in FIG. 18E. That is, dispensing the luminescent reagent 303 into the well Wb is performed through the nozzle 140, as depicted in FIG. 18E. At this time, luminescence measurement by the luminescence measurement unit 120 is not performed.

(B7) Then, the movement controller 211 horizontally moves the stage 101. At this time, the stage 101 is horizontally moved to perform dispensing the reagent into the well Wd, skipping the well Wc adjacent to the well Wb into which the reagent is dispensed at (B6). Note that the well Wc is already dispensed with the luminescent reagent 303 at (B2). That is, dispensing the luminescent reagent 303 into the well Wd is performed through the nozzle 140, as depicted in FIG. 18F, and, at the same time, a measurement is performed of luminescence produced by the mixture liquid 302 in the well Wb into which the reagent is dispensed at (B6).

(B8) Then, horizontally moving the stage 101 is performed by the movement controller 211. At this time, the stage 101 is horizontally moved skipping the well We adjacent to the well Wd into which the reagent is dispensed at (B7) to perform, dispensing the reagent into a well Wf. Note that the luminescent reagent 303 is already dispensed into the well We at (B3). That is, dispensing the luminescent reagent 303 into the well Wf is performed through the nozzle 140, as depicted in FIG. 18G, and, at the same time, a measurement is performed of luminescence produced by the mixture liquid 302 in the well Wd into which the reagent is dispensed at (B7).

(B9) After several steps, dispensing the reagent into a well Wj located near the terminal side of the microplate M is performed through the nozzle 140, as depicted in FIG. 18H, and a measurement is performed by the luminescence measurement unit 120 of luminescence in a well Wh into which the reagent is dispensed preceding the well Wj.

(B10) After that, a measurement is performed of luminescence produced by the mixture liquid 302 in the well Wi into which the reagent is dispensed in (B9). At this time, dispensing through the nozzle 140 is not performed.

As depicted in FIGS. 18A through 18H, the fourth embodiment performs dispensing and luminescence measurement every other well. Dispensing and luminescence measurement performed every other well as described above allows to prevent crosstalk from occurring at the well W into which the reagent is being dispensed in the luminescence measurement step. This allows a high accuracy of luminescence measurement.

It would be understandable that dispensing and luminescence measurement are performed every other well, as in FIGS. 18A through 18H; the present invention, however, is not limited thereto. Dispensing and luminescence measurement may be performed at intervals of every three well, every four wells, and the like between a well W into which the reagent is dispensed and a well W for which luminescence measurement is performed.

Fifth Embodiment

Figure 19:
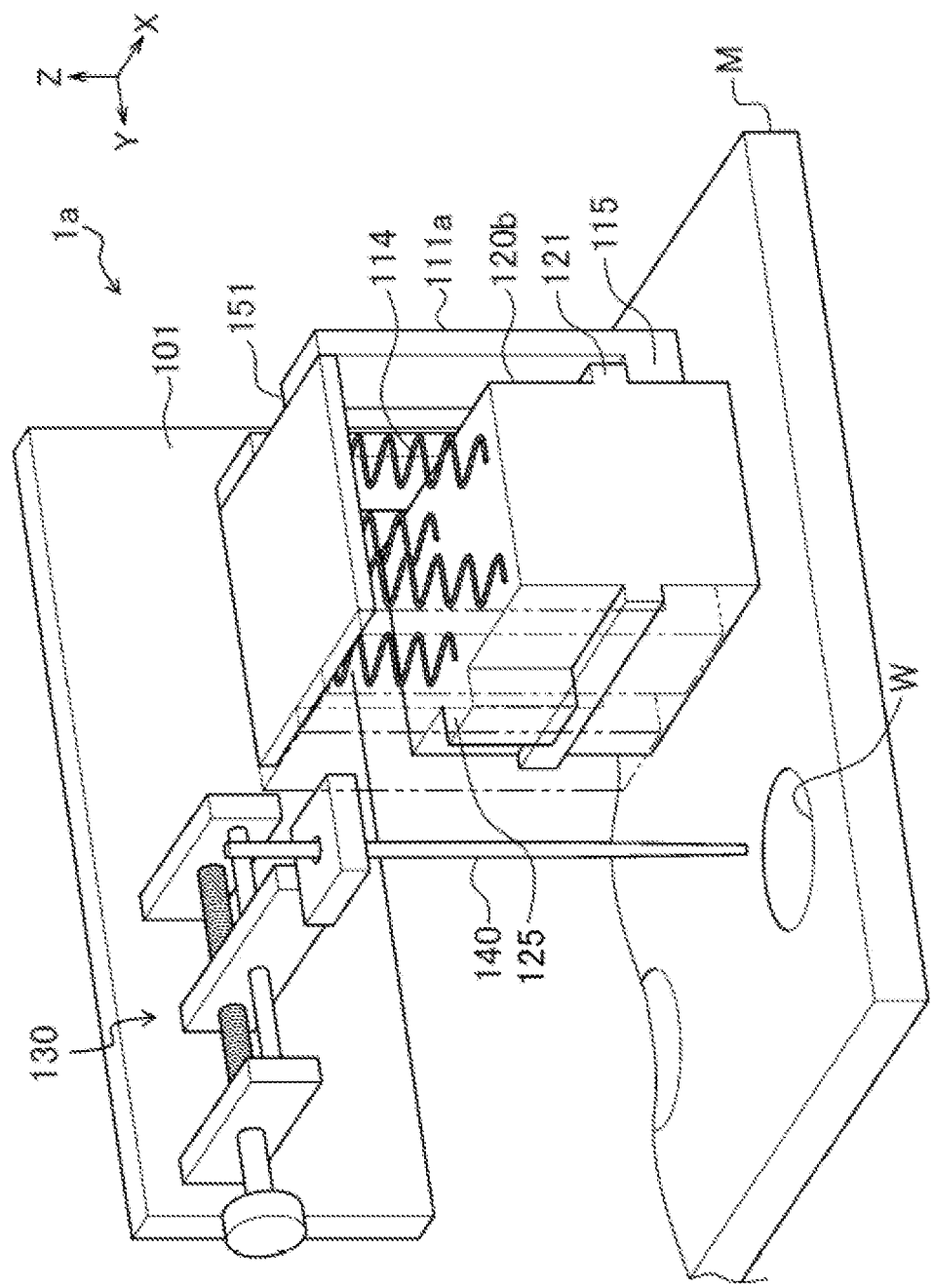
FIG. 19 is an external view depicting a modified example of a chemiluminescence measurement apparatus.

FIG. 19 is an external view of a chemiluminescence measurement apparatus 1a according to a fifth embodiment. Additionally, FIG. 20 is a top view of the chemiluminescence measurement apparatus 1a, when viewed in a z-axis direction in FIG. 19, and FIG. 21 is a side view of the chemiluminescence measurement apparatus 1a, when viewed in a Y-axis direction in FIG. 19.

Figure 20:
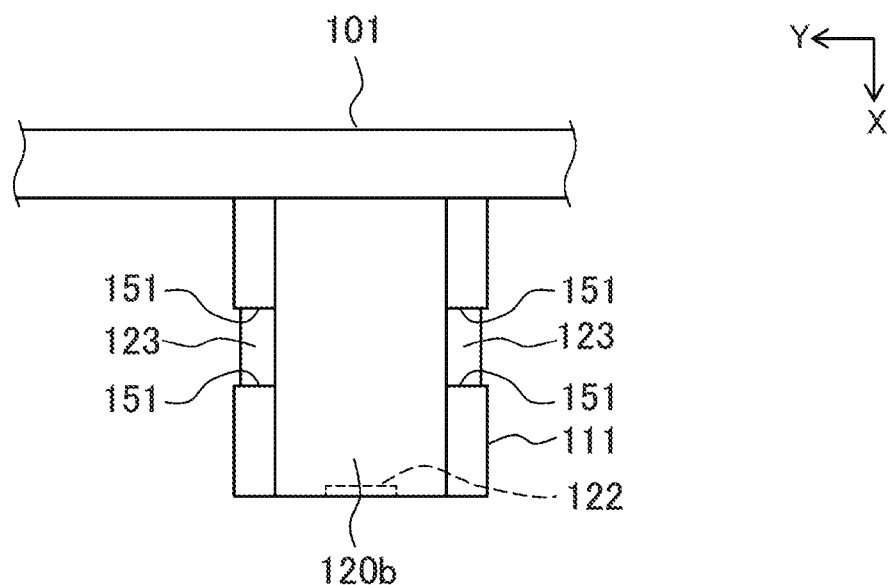
FIG. 20 is a top view depicting the modified example of the chemiluminescence measurement apparatus.
Figure 21:
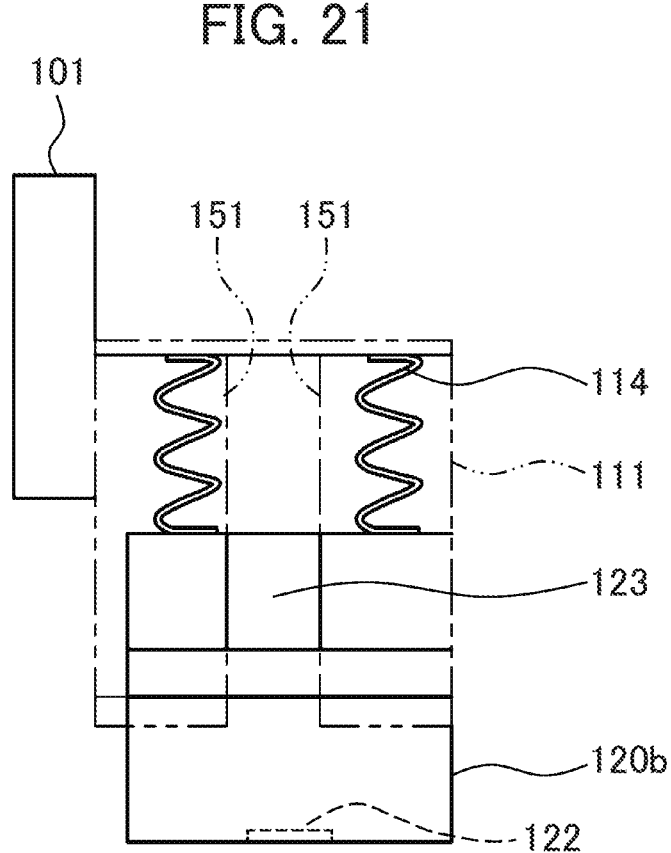
FIG. 21 is a side view depicting the modified example of the chemiluminescence measurement apparatus.

In FIGS. 19 through 21, components corresponding to those in FIGS. 1 through 3 are assigned identical reference numerals and omitted to be described.

In the chemiluminescence measurement apparatus 1a depicted in FIGS. 19 through 21, the supporting posts depicted in FIGS. 1 through 3 are removed and second protrusions 125 (sliding portions) are provided in lateral surfaces of the luminescence measurement unit 120b. Furthermore, the holder 11 is provided with recesses (sliding portions) 151 in positions matching the second protrusions 125. The second protrusions 125 slide along the recesses 151 to guide a vertical move of the luminescence measurement unit 120b. Such a structure provides the same effect as that of the first embodiment.

The chemiluminescence measurement apparatus 1 may be equipped with plural nozzles 140.

Further, the chemiluminescence measurement apparatus 1 is covered with a cover or the like which is not depicted, which allows to prevent crosstalk caused by light in a room.

Note that the springs 114 may be omitted in both the first and second embodiments.

Furthermore, the embodiments may be provided with plural nozzles 140 and plural luminescence measurement units 120. In this case, the number of the nozzles 140 is preferably equal to the number of the luminescence measurement units 120, which allows to perform dispensing a luminescent reagent and luminescence measurement for wells W arranged in plural lines at the same time.

Note that the present invention is not limited to the embodiments described above and includes various modifications. For example, the above-described embodiments are described in detail to explain the present invention clearly and the invention is not necessarily limited to those including all components described. Further, a subset of components of an embodiment may be replaced by one or more components of another embodiment and a subset of components of an embodiment may be added with one or more components of another embodiment. Furthermore, for a subset of the components of each embodiment, other components of the embodiment may be added thereto or replace the subset, or the subset may be deleted.

Besides, a subset or all of the aforementioned components, functions, each unit 210 to 213, or the like, may be implemented by hardware; for example, by a design of an integrated circuit. Also, the aforementioned components, functions, and the like, as depicted in FIG. 5, may be implemented by software in such a way that a processor such as the CPU 202 interprets and executes programs that implement the respective functions. The programs implementing the respective functions, and information represented in tables, files, and the like may be stored in an HD (Hard Disk) and, besides, in a recording device such as a memory or an SSD (Solid State Drive) or a portable recording medium such as an IC (Integrated Circuit) card, an SD (Secure Digital) card, or a DVD (Digital Versatile Disc).

Moreover, in each of the embodiments, control lines and information lines which are considered as necessary for explanation are delineated and all control lines and information lines involved in a product are not necessarily delineated. Actually, almost all components may be considered to be interconnected.

REFERENCE SIGNS LIST 1, 1a: chemiluminescence measurement apparatus
2: control device (control unit)
101: stage (moving unit)
114: spring
120, 120a, 120b: luminescence measurement unit
122: photosensitive portion
122a: photosensitive surface
121: first protrusion (sliding portion)
124: rubber portion (cushion portion)
125: second protrusion (sliding portion)
130: nozzle position adjusting part
140: nozzle
151: recess (sliding portion)
160: nozzle position sensor (detector)
303: luminescent reagent (liquid)
400: plate mask
403: rubber portion (cushion portion)
D: deck
M: microplate
W, Wa through Wj: well

We claim:

1. A luminescence measurement system comprising:
a nozzle for dispensing a liquid into wells in a microplate;
a luminescence measurement unit configured for measuring luminescence occurring in the wells;
a moving unit to move the nozzle and the luminescence measurement unit together vertically and horizontally; and
a control unit,
wherein:
the nozzle is secured to the moving unit;
the luminescence measurement unit is mounted to be movable vertically with respect to the moving unit;
the nozzle is placed in a position in which a height of a lowest point of the nozzle is higher than a lowest point of the luminescence measurement unit before they are set over the respective wells; and
the control unit is programmed to perform:
a first moving down step of moving the moving unit down;
a second moving down step of moving the moving unit further down until a bottom end of the nozzle is set in a predetermined position even after a bottom end of the luminescence measurement unit contacts a deck of the microplate; and
a measurement and dispensing step of measuring luminescence by the luminescence measurement unit while dispensing the liquid through the nozzle.

2. The luminescence measurement system according to claim 1,
comprising a detector configured to detect a distance between the nozzle and a liquid surface or a distance between the nozzle and the microplate; and wherein
the control unit is programmed to perform a moving down of the moving unit until the bottom end of the nozzle is arrived at a predetermined position, based on the distance detected by the detector from the nozzle to the liquid surface or the microplate.

3. A luminescence measurement method performed by a luminescence measurement system, the luminescence measurement system comprising:
a nozzle for dispensing a liquid into wells in a microplate;
a luminescence measurement unit for measuring luminescence occurring in the wells;
a moving unit to move the nozzle and the luminescence measurement unit together vertically and horizontally; and
a control unit,
wherein:
the nozzle is secured to the moving unit;
the luminescence measurement unit is mounted to be movable vertically with respect to the moving unit;
the nozzle is placed in a position in which a height of a lowest point of the nozzle is higher than a lowest point of the luminescence measurement unit before they are set over the respective wells; and
the method comprising steps performed by the system controlled by the control unit:
a first moving down step of moving the moving unit down;
a second moving down step of moving the moving unit further down until a bottom end of the nozzle is set in a predetermined position even after a bottom end of the luminescence measurement unit contacts a deck of the microplate; and
a measurement and dispensing step of measuring the luminescence by the luminescence measurement unit and at a same time dispensing the liquid through the nozzle.

4. The luminescence measurement method according to claim 3,
the method comprising steps performed by the system controlled by the control unit:
a first suction step of sucking in air of a predetermined volume after discharging a liquid from the nozzle;
a discharging step of discharging a liquid having a liquid volume to be dispensed plus the predetermined volume from the nozzle when dispensing the liquid into each of the wells; and
a second suction step of sucking in a liquid of the predetermined volume after the discharging.

5. The luminescence measurement method according to claim 3,
wherein the control unit moves the microplate horizontally in a direction opposite to a moving direction of the moving unit when moving the moving unit horizontally.

* * * * *